United States Patent

Tseng

Patent Number: 6,033,417
Date of Patent: Mar. 7, 2000

[54] SAFE ROLL—SCRAPING EAR PICK

[76] Inventor: Shao-Chien Tseng, No. 130 Sec. 2, Yang-Shin Rd., Yang-Mei Taoyuan 326, Taiwan

[21] Appl. No.: 09/348,992

[22] Filed: Jul. 7, 1999

[51] Int. Cl.[7] .................................................. A61F 9/00
[52] U.S. Cl. ............................................. 606/162; 606/106
[58] Field of Search ............................... 606/1, 106, 107, 606/110, 113, 127, 159, 160, 161, 162; 604/19, 22, 187

[56] References Cited

U.S. PATENT DOCUMENTS

| | | | |
|---|---|---|---|
| 320,889 | 6/1885 | Ruoff | 606/162 |
| 1,326,616 | 12/1919 | Schuller | 606/162 |
| 2,617,409 | 11/1952 | Biederman | 606/162 |
| 5,496,338 | 3/1996 | Miyagi et al. | 606/162 |
| 5,632,756 | 5/1997 | Kruglick | 606/162 |
| 5,868,754 | 2/1999 | Levine et al. | 606/108 |
| 5,888,199 | 3/1999 | Karell et al. | 606/162 |
| 5,897,568 | 4/1999 | Vanraes | 606/162 |

FOREIGN PATENT DOCUMENTS

| | | | |
|---|---|---|---|
| 604145 | 10/1934 | Germany | 606/162 |
| 3633585 | 4/1988 | Germany | 606/162 |

*Primary Examiner*—Glenn K. Dawson
*Attorney, Agent, or Firm*—Pro-Techtor International Services

[57] ABSTRACT

A safe roll-scraping ear pick includes a stick, a seat as well as a screw spring set including an exterior screw spring and an interior screw spring is disclosed. The stick is provided on one end thereof with the seat; the screw spring set is slipped over the seat. Thereby, rings on the exterior screw spring of the screw spring set all have chances to contact a wall of an ear. By rolling to and fro of the stick, the multiple rings can scrape and remove ear wax. This can increase efficiency of cleaning with the safety of non-damage to the tissue of ears.

3 Claims, 5 Drawing Sheets

SAFE ROLL—SCRAPING EAR PICK

BACKGROUND OF THE INVENTION

1. Field of the invention

The present invention is related to a safe roll-scraping ear pick, and especially to an ear pick having a stick provided on one end thereof with a screw spring set. A screw spring exposed exteriorly of the screw spring set and spreading in a radiation mode can scrap and remove ear wax by rolling. Thereby, a function of tender and safe scraping as well as removing ear wax can be obtained.

2. Description of the Prior Art

As is well known, the inner walls of ears of people tend to produce and accumulate ear wax, people are accustomed to remove ear wax with ear picks to keep cleanliness and sanitation of ears.

It has been known that conventional ear pick products used for a very long time are in the form of sticks, i.e., each has on one end of a stick a curved small dipper in benefit to removing of ear wax in the cavity of the ear. The periphery of the curved small dipper is mostly sharper, while the tissue in the ear is quite weak and sensitive; when the curved small dipper of the ear pick scraps and removes ear wax, it is often that an undue force hurts the interior of the ear. And even worse, it may damage the hearing tissue of the ear and thus badly influences hearing ability.

And more, the inner wall of an ear has irregular curvature, while the ear pick has the curved small dipper, whenever it is used to remove ear wax, the contact angle between the wall and the curved small dipper varies and tender scraping can hardly be acquired. The object of removing of ear wax can almost be done by deeply extending the ear pick into the cavity of the ear to do several times of ear wax scraping. However, such several times of ear wax scraping can not give correct judgement of whether the position to be scraped is right and the ear wax has been completely removed. Even when the ear wax has been removed, the debris left during ear wax scraping must be wiped off with a cotton stick to get more complete cleaning. In view of this, using of an ear pick is not smooth and inconvenient, and effect of removing thereof is hardly that evident.

SUMMARY OF THE INVENTION

The object of the present invention is to provide a convenient, effective and safe ear pick in order to increase convenience in removing ear wax and efficiency of cleaning with the safety of non-damage to the tissue of ears.

In the present invention, a stick is provided on one end thereof with a seat in which a screw spring set including an exterior screw spring and an interior screw spring is provided. The exterior screw spring of the screw spring set in this structure is spreading in a radiation mode to leave a gap between every two rings thereof. Thereby, the rings of the exterior screw spring can be used to scrape the inner wall of an ear tenderly, and the stick is rolled to and fro to render the exterior screw spring to remove ear wax by rolling. In this way, ear wax can be effectively cleared out of the ear, and force is uniformly exerted on each ring of the exterior screw spring. Therefore, the situation that an undue force hurts the interior of the ear can be avoided.

The present invention will be apparent after reading the detailed description of the preferred embodiment thereof in reference to the accompanying drawings.

DETAILED DESCRIPTION OF THE PREFERRED EMBODIMENT

Figure 1:
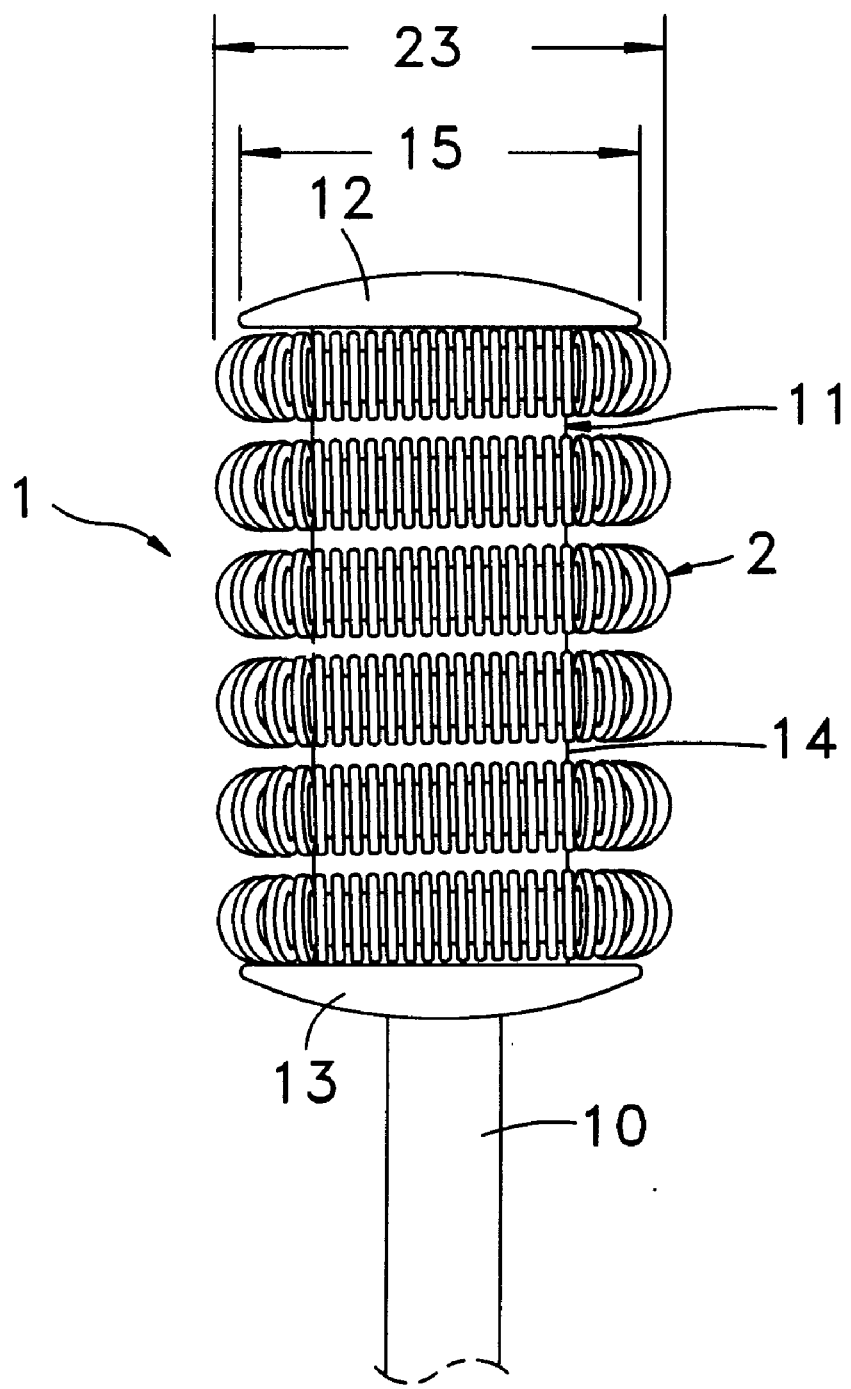
FIG. 1 is a front view showing the ear pick of the present invention.

Referring to FIG. 1, the present invention provides a safe roll-scraping ear pick 1 comprised mainly of a stick 10, a seat 11 as well as a screw spring set 2 including an exterior screw spring 20 and an interior screw spring 21.

Figure 2:
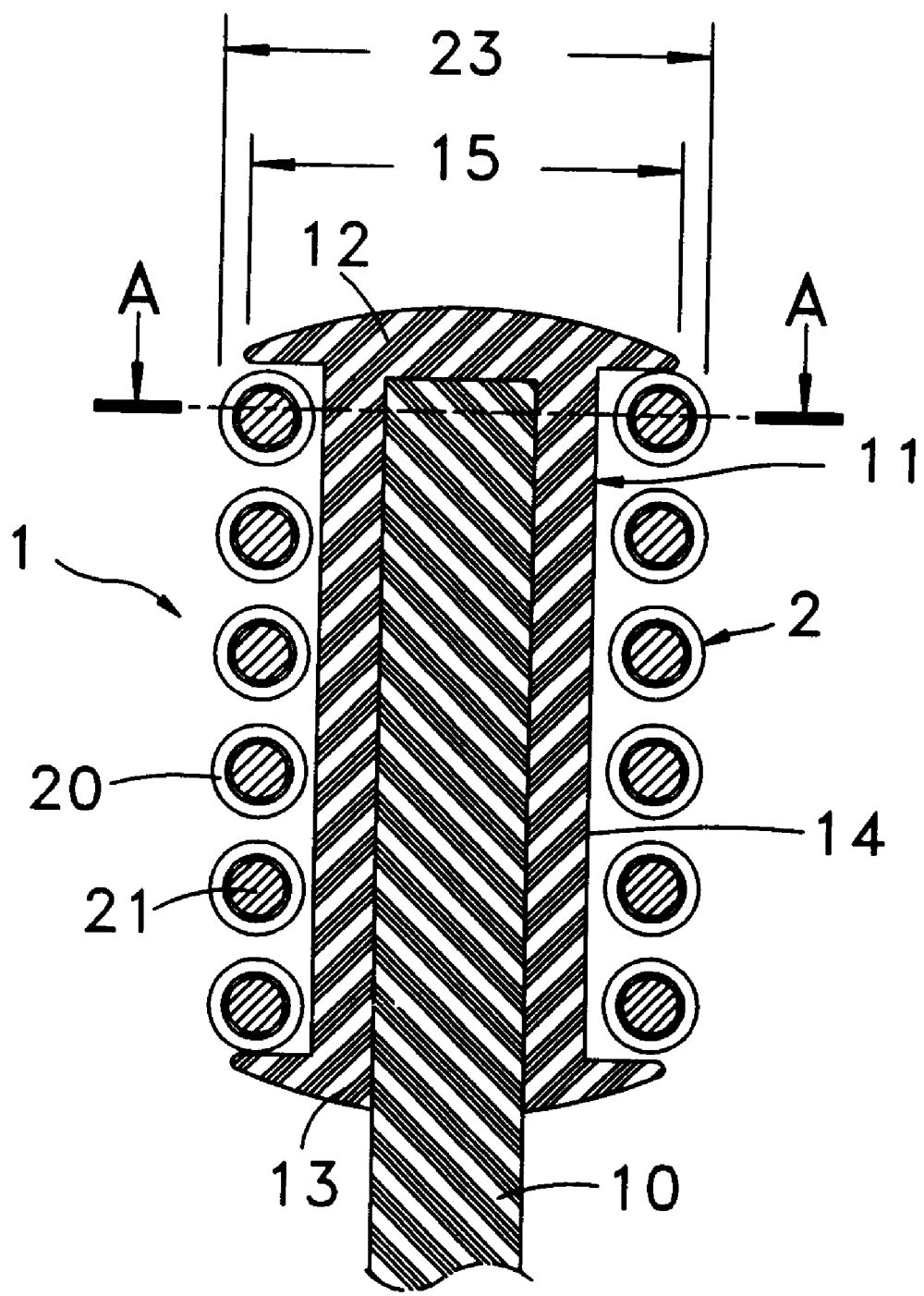
FIG. 2 is a sectional view of the ear pick of the present invention.

Wherein, the stick 10 is provided on one end thereof with the seat 11. The seat 11 is made integrally of soft plastic (as shown in FIG. 2), or is assembled from two engaging seat components engaged with each other. The seat 11 is formed to have two soft stop ends 12, 13, and a neck portion 14 between the ends 12, 13. The neck portion 14 is for mounting of the screw spring set 2 thereover (FIG. 2), thus the structure of the safe roll-scraping ear pick 1 is completed.

Figure 3:
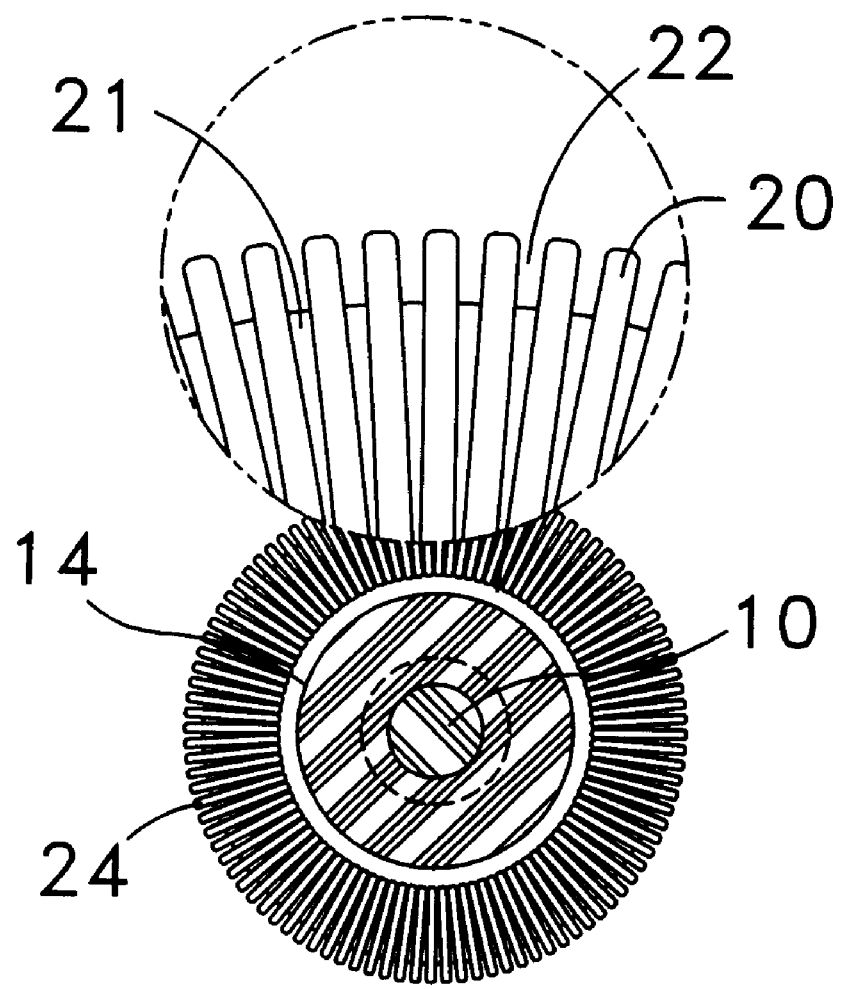
FIG. 3 is an enlarged view of an area taken from the sectional line A—A from FIG. 2.

The screw spring set 2 includes the exterior screw spring 20 and the interior screw spring 21 (as shown in FIG. 2 and 3). Before the screw spring set 2 is mounted on the neck portion 14, the interior screw spring 21 is loosely fitted over with the exterior screw spring 20 to form the screw spring set 2. And then the screw spring set 2 snap engages in position on the neck portion 14 of the seat 11. Wherein, the diameter 23 of the exterior screw spring 20 is larger than the widths 15 of the stop end 12, 13, of the seat 11 (FIG. 2). The exterior screw spring 20 is slipped over the screw threads of the interior screw spring 21. So that each ring 24 of the exterior screw spring 20 is spreading in a radiation mode about a center of a cylinder and a gap 22 is left between every two rings 24 (FIG. 3). Thereby, the rings 24 of the exterior screw spring 20 can be used to scrape the inner wall of an ear tenderly, and the stick 10 is rolled to and fro to render the smooth and curved exterior screw spring 20 to scrape ear wax.

Figure 4:
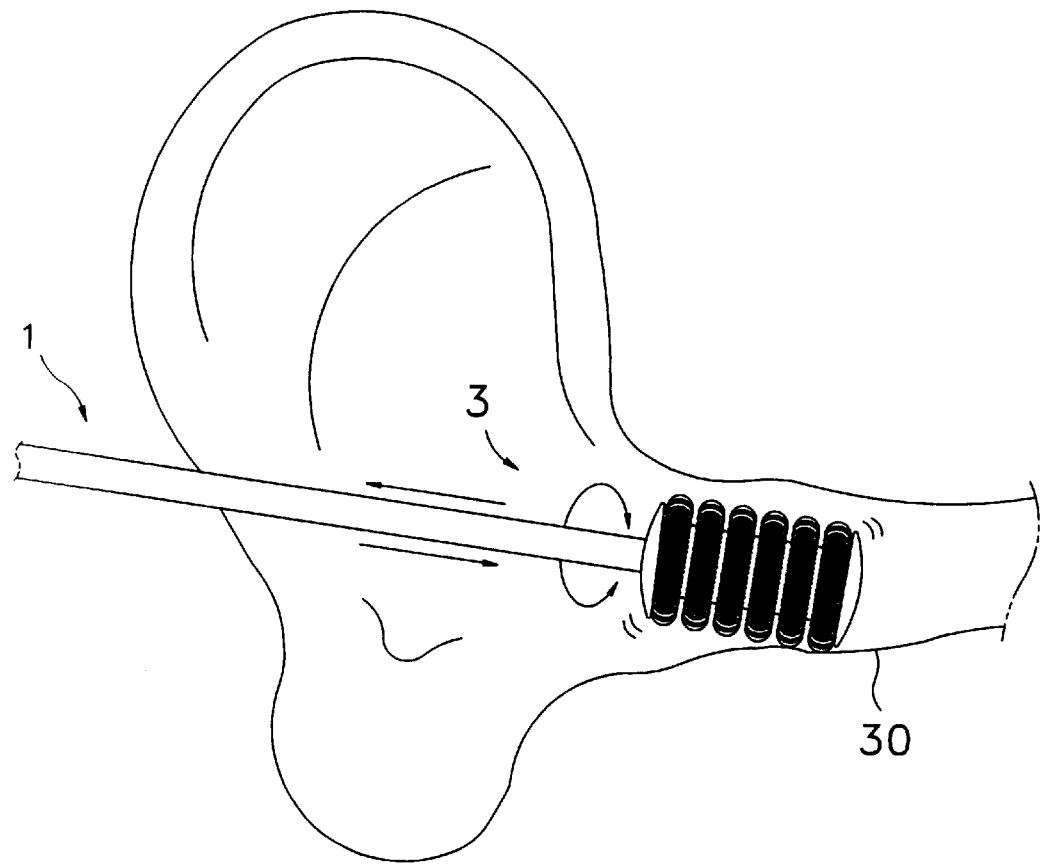
FIG. 4 is a schematic view showing operation of the ear pick of the present invention.

When in use, the stick 10 is extended into the cavity 3 of the ear having irregular curvature (as shown in FIG. 4); the rings 24 of the exterior screw spring 20 all have chances to contact a wall 30 of the ear. The contact angles between the wall 30 and the rings 24 all are nearly right angles. Therefore, by rolling to and fro of the stick 10, the multiple rings 24 can scrape and remove ear wax. The gaps 22 left between every two rings 24 are used to take away the debris left during ear wax scraping to enhance effect of cleaning. When overly large force is exerted during operation of the ear pick 10, the exterior screw spring 20 can scatter stress of the force through its elastic nature and another spring 21. The force thereby can be uniformly distributed to other rings 24 of the exterior screw spring 20 and the interior screw spring 21 to avoid damage to the wall 30 of the ear by undue force.

Figure 5:
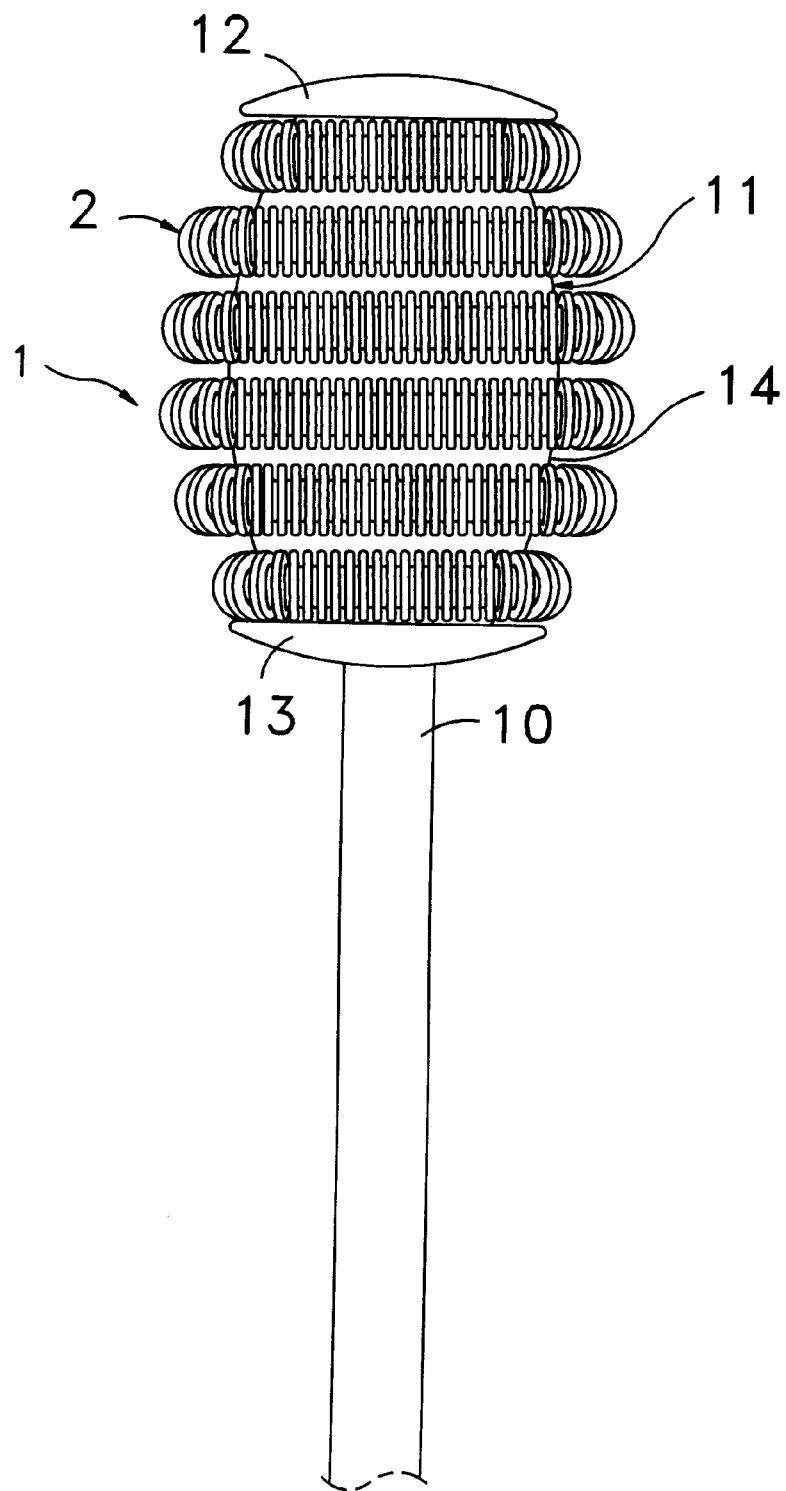
FIG. 5 shows another embodiment of ear pick of the present invention.

Further in practice of the present invention, the neck portion 14 of the seat 11 can also be formed a curved convex cylinder wall. So that when the screw spring set 2 snap engages in position on the neck portion 14, it surrounds the latter and is also in a shape of a curved convex cylinder (as shown in FIG. 5). And more, the exterior screw spring 20 and the interior screw spring 21 can be made from spring wires of stainless steel, or can be made from nylon wires.

In conclusion, the safe roll-scraping ear pick of the present invention can increase the effect of cleaning, can effectively avoid the trouble of damage to the wall in the cavity of an ear by undue force.

Having thus described the technical structure of my invention with practicability and improvement, therefore, what I claim as new and desire to be secured by Letters Patent of the United States are:

1. A safe roll-scraping ear pick comprising a stick, a seat and a screw spring set including an exterior screw spring and an interior screw spring, wherein, said stick is provided on one end thereof with said seat; said seat is formed to have two soft stop ends and a neck portion between said stop ends, said safe roll-scraping ear pick is characterized by:

said exterior screw spring is slipped over said interior screw spring to form said screw spring set;

said screw spring set is slipped over said neck portion and is positioned by said two soft stop ends, the diameter of said exterior screw spring is larger than the widths of said stop ends, rings of said exterior screw spring spread in a radiation mode on said seat.

2. A safe roll-scraping ear pick as in claim 1, wherein, said neck portion on said seat is formed by a curved convex cylinder wall, so that when said screw spring set snap engages in position on said neck portion, said screw spring set surrounds said neck portion and is also in a shape of a curved convex cylinder.

3. A safe roll-scraping ear pick as in claim 1, wherein, said exterior screw spring and said interior screw spring of said screw spring set are made from spring wires of stainless steel, or made from nylon wires.

* * * * *